United States Patent [19]

Mueller et al.

[11] Patent Number: 5,019,597

[45] Date of Patent: May 28, 1991

[54] BICYCLOALKYL TRICYCLOALKYL, AZABICYCLOALKYL AND AZATRICYCOALKYL AMIDES

[75] Inventors: Richard A. Mueller, Glencoe; Richard A. Partis, Evanston; James R. Deason, Wilmette, all of Ill.

[73] Assignee: G. D. Searle & Co., Skokie, Ill.

[21] Appl. No.: 79,731

[22] Filed: Jul. 30, 1987

Related U.S. Application Data

[63] Continuation of Ser. No. 819,761, Jan. 21, 1986, abandoned, which is a continuation-in-part of Ser. No. 809,954, Dec. 20, 1985, abandoned, which is a continuation-in-part of Ser. No. 698,050, Feb. 4, 1985, abandoned.

[51] Int. Cl.$^5$ .................. A61K 31/165; C07C 321/00
[52] U.S. Cl. ...................... 514/618; 564/162
[58] Field of Search .................. 564/162; 514/618

[56] References Cited

U.S. PATENT DOCUMENTS

| | | | |
|---|---|---|---|
| 3,392,194 | 7/1968 | Waring | 564/162 X |
| 3,624,143 | 11/1971 | Shen et al. | 564/162 X |
| 3,652,646 | 3/1972 | Leigh et al. | 564/162 X |
| 4,534,874 | 8/1985 | Steinberg et al. | 564/139 X |

FOREIGN PATENT DOCUMENTS 57-58663  4/1982  Japan ................... 564/162

Primary Examiner—Carolyn S. Elmore
Attorney, Agent, or Firm—Mary J. Kanady; Paul D. Matukaitis

[57] ABSTRACT

The compounds of this invention are bicyclic, tricyclic, azabicyclic and azatricyclic amides represented by the formula:

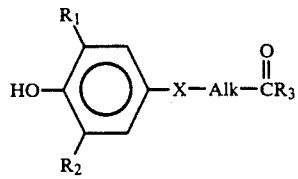

wherein: $R_1$ and $R_2$ are the same or different members of the group consisting of halo, phenyl, substituted phenyl and a

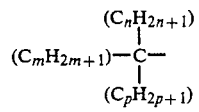

group wherein n, m and p are independently an integer of from 1 to 8 provided that $n+m+p$ is equal to or less than 10; X is thio, sulfinyl or sulfonyl; Alk is straight or branched chain lower alkylene; $R_3$ is selected from the group consisting of a bicycloalkylamino, tricycloalkylamino, azabicycloalkyl, azatricycloalkyl, azabicycloalkylamino, azatricycloalkylamino or dicycloalkylamino. The compounds are useful as anti-inflammatory and anti-allergy agents.

13 Claims, No Drawings

BICYCLOALKYL TRICYCLOALKYL, AZABICYCLOALKYL AND AZATRICYCOALKYL AMIDES

This is a continuation of application Ser. No. 06/819,761, filed Jan. 21, 1986 which is a continuation-in-part of application Ser. No. 06/809,954 filed Dec. 20, 1985 which was a continuation-in-part of application Ser. No. 06/698,050 filed Feb. 4, 1985 all abandoned.

BACKGROUND OF THE INVENTION

A. Field of the Invention

The present invention relates to novel hindered amides and more particularly relates to multicycloalkyl and azamulticycloalkyl amides which are 5-lipoxygenase inhibitors and are useful as anti-inflammatory and anti-allergy agents.

It is well recognized that arachidonic acid and its analogs, unsaturated fatty acids, are the precursors of prostaglandins, thromboxanes, the 5-, 11-, 12- and 15-hydroxyeicosatetraenoic acids (HETEs, DIHETEs, TRIHETEs) and hydroperoxyeicosatetraenoic acids (HPETEs) and the leukotrienes, all of which have profound physiological effects. The leukotrienes, which are produced via the 5-lipoxygenase pathway, are the major contributors to the onset of the symptoms of asthma, and mediators for immediate hypersensitivity reactions and inflammation.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other immediate hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, $D_5$ and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in inflammatory bowel disease.

Chemotaxis is a reaction by which the direction of migration of cells is determined by substances in their environment. It is one of the major processes bringing leukocytes from the blood to an inflammatory site. Whether the inflammation is caused by an infectious agent, allergic challenge, or other pro-inflammatory stimuli. $LTB_4$ is not only chemotactic for neutrophils and monocytes, but is also highly active in stimulating eosinophil locomotion. The infiltration of eosinophils is one of the histologic features of a variety of allergic reactions.

With the exception of benoxaprofen, which has 5-lipoxygenase inhibition activity, aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid. These prostaglandin synthetase inhibitors generally exhibit anti-inflammatory, anti-pyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced pro-inflammatory effects. Administration of the NSAIDs alone can produce allergic reactions including bronchospastic reactivity; skin rashes; syndrome of abdominal pain, fever, chills, nausea and vomiting, and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs.

Prior to the recognition of the arachidonic acid cascade and the significance and interaction of the 5-lipoxygenase and other arachidonic acid cascade conversion products in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides multicycloalkyl and azamulticycloalkyl amides which are metabolically stable inhibitors of the 5-lipoxygenase pathway and are useful in the treatment of asthma and other allergy and hypersensitivity reactions, and many types of inflammation.

To date, benoxaprofen has been the only commercial anti-inflammatory agent which has 5-lipoxygenase inhibition activity. Prior to its withdrawal from the market because of untoward side effects, benoxaprofen was considered to represent a significant advance in the treatment of crippling arthritis and psoriasis. Thus, there remains a longstanding need for agents which block the mechanisms responsible for inflammation and allergic reactions, and which can be safely employed to treat, for example, arthritis, asthma, psoriasis and other dermatoses, allergic reactions and other 5-lipoxygenase mediated conditions. A need also exists for agents which can be administered with the inhibitors of other lipoxygenase enzymes, e.g. cyclooxygenase, to mitigate their side effects and support their desirable medicinal properties.

See Bengt Samuelson, "Leukotrienes: Mediators of Immediate Hypersensitivity Reactions and Inflammation", *Science*, Vol. 220, pp. 568–575 (May 1983); Michael K. Bach, "Inhibitors of Leukotriene Synthesis and Action", *The Leukotrienes, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York, 1984); Editorial, "Leukotrienes and other Lipoxygenase Products in the Pathegonesis and Therapy of Psoriasis and Dermatoses", *Arch. Dermatol.*, Vol. 119, pp 541–547 (July, 1983); Robert A. Lewis et al., "A Review of Recent Contributions on Biologically Active Products of Arachidonate Conversion", *Int. J. Immunopharmac.*, Vol. 4, No. 2, pp 85–90 (1982); Michael K. Bach, *Biochemical Pharmacology*, Vol. 23, No. 4, pp 515–521 (1984); E. L. Becker, *Chemotactic Factors of Inflammation*, pp 223–225 (Eliver Science Publishers B.V., Amsterdam, 1983); P. Sharon and W. F. Stenson, *Gastroenterology*, Vol. 84, 454 (1984); and M. W. Musch, et al., *Science*, Vol. 217, 1255 (1982).

The present invention provides compounds which block the 5-lipoxygenase pathway of the arachidonic acid cascade, block the formation of the leukotrienes therefore responsible for the allergy and inflammation, and hence and represent a new class of therapeutic agents which are useful in the treatment of allergic and hypersensitivity reactions and inflammation, alone, or in combination with other oxygenase inhibitors such as the non-steroidal anti-inflammatory agents (cyclooxygenase inhibitors).

B. Prior Art

Wagner et al. U.S. Pat. No. 4,029,812, and related U.S. Pat. Nos. 4,076,841 and 4,078,084, which issued from divisional applications of the -812 application all assigned to The Dow Chemical Company, disclose 2-(3,5-di-tert-butyl-4-hydroxyphenyl)thiocarboxylic acids, esters and simple amides which are hypolipidemics and are useful in reducing plasma lipid levels, especially cholesterol and triglyceride levels.

The Wagner et al. and related compounds have also been reported in the literature as plasticizers and pesticides. See for Example, *Khim. Tekhnol.* 20(4), 568–574 (1977); *Pestic. Biochem. Physiol.* 1979, 12(1), 23–30. *Chem. Abs.* 90(19):151802x is of interest.

SUMMARY

The compounds of this invention are sterically hindered multicyclic amides represented by the formula

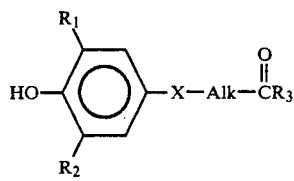

wherein: $R_1$ and $R_2$ are the same or different members of the group consisting of halo, phenyl, substituted phenyl and a

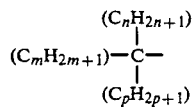

group wherein n, m and p are independently an integer of from 1 to 8 provided that $n+m+p$ is equal to or less than 10; X is thio, sulfinyl or sulfonyl; Alk is straight or branched chain lower alkylene, and $R_3$ is selected from the group consisting of a bicycloalkylamino, tricycloalkylamino, azabicycloalkyl, azatricycloalkyl, azabicycloalkylamino, azatricycloalkylamino or dicycloalkylamino.

The compounds of the present invention are useful in the treatment of allergy and hypersensitivity reactions and inflammation. The compounds are particularly useful in the treatment of arthritis and other inflammatory joint disease, asthma, proliferative skin disease such as psoriasis, and the like, alone or in combination with one or more cyclooxygenase inhibitors.

DETAILED DESCRIPTION OF PREFERRED EMBODIMENTS

The compounds of the present invention are generally administered in oral or parenteral dosages of from 0.1 to 100 mg/kg, preferably 0.5 to 50 mg/kg daily, preferably in divided dosages, to patients suffering from allergic or hypersensitivity reactions or inflammation, and are preferably applied topically to patients suffering from proliferative skin disease such as psoriasis. The compounds may be administered as the sole therapeutic agent, or in combination with other agents such as cyclooxygenase inhibitors, particularly in patients who exhibit pro-inflammatory or allergic response to, for example, conventional non-steroidal anti-inflammatory agents. Parenteral, e.g., intravenous, administration is preferable if a rapid response is desired, as, for example, in some cases of asthma.

Generally speaking, synthesis of the compounds of this invention is accomplished by displacement of the halogen or tosylate on a halo or tosyl substituted aliphatic acyl multicyclic or azamulticyclic amide by a thiol in the presence of a base. Addition of a thiol to the double bond of a suitable alkenyl acyl amide is also a useful synthetic route. Alternatively, the displacement via reaction with a thiol and base can be carried out on a tosyl or halo substituted aliphatic carboxylic acid or ester which is then converted into the amide via reaction of the corresponding acid chloride with the desired multicyclic amine. An ester is preferably hydrolized to the corresponding acid before conversion to the acid chloride by, for example, oxalyl chloride. The sulfones and sulfoxides are readily prepared by oxidation of the sulfides with, for example, m-chloroperbenzoic acid or sodium metaperiodate.

Suitable amines include, but are not limited to, N-tricyclo[3.3.1.1$^{3,7}$]dec-1-yl amine; N-[6,6-dimethylbicyclo[3,1,1]hept-2-yl amine; N-endo-bicyclo[2,2,1]hept-2-yl amine; N-tricyclo [3.3.1.1$^{3,7}$]dec-2-yl amine; N,N-dicyclohexylamine, 3-azabicyclo[3.2.2]nonane; N-[1-azabicyclo[2,2,2]octa-3-yl amine; 3-azabicyclo[3.3.2] nonane; 4-azatricyclo[4.4.0.0$^{3,8}$]decane; 4-azatricyclo [4.3.1.1$^{3,8}$]undecane; 11-azabicyclo[4.4.1]undecane; 3-amino-9-azabicyclo[3.3.1]nonane; 2-aminobicyclo[2.2.1-]heptane; 2-amino-1,7,7-trimethylbicyclo[2.2.1]heptane; 1-amino-2-azatricyclo[3.3.1.1$^{3,7}$]decane; and the like. The above lipophilic hindered amines are C-bridged cycloalkylamines and C-bridged azacycloalkylamines.

The term "lower alkyl", as used herein, refers to straight or branched chain lower alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "lower alkylene", as used herein, refers to straight or branched chain lower alkylene groups having from 1 to 6 carbon atoms, i.e., methylene, ethylene, n-propylene, iso-propylene, n-butylene, sec-butylene, 1,1-dimethylethylene, n-pentylene, 2-methylbutylene, 2,2-dimethylpropylene, n-hexylene and the like.

The group represented by X is preferably thio or sulfinyl and most preferably thio.

Preferred radicals represented by the group of the formula

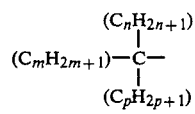

include tertiary alkyl moieties wherein n and m are preferably 1 or 2 and most preferred radical is represented by the group wherein n, m and p are 1, namely t-butyl.

The term "halo", as used herein, included chloro, bromo, fluoro and iodo.

The term "lower alkoxy" refers to alkoxy groups having from 1 to 6 straight or branched chain carbon atoms, i.e., methoxy, ethoxy, n-propoxy, tert-butoxy, etc.

The term "substituted phenyl" refers to phenyl having one or more substituents selected from the group consisting of amino, halo, hydroxy, lower alkyl, lower alkylaminoalkyl, lower dialkylaminoalkyl, trifluoromethyl, lower alkoxy, and the like for $R_1$ and $R_2$.

The selective activity of the compounds of this invention was first determined using the following assays.

Test A- An in vitro inhibition of soybean 15-lipoxygenase assay is employed to check the specificity of selected 5-lipoxygenase inhibitors. The oxygen-uptake during the oxidation of arachidonic acid to 15-HPETE by soybean lipoxygenase is measured in the presence and absence of inhibitors, using nordihydroguaiaretic acid (NDGA) as a reference standard. Compounds which inhibit at 100 $\mu$M are tested further to determine the $IC_{50}$ values. "IC" stands for "inhibitory concentration".

Test B- Determination of anti-inflammatory, anti-allergy activity: in vitro inhibition of 5-lipoxygenase. The 100,000 $\times$g supernatant fraction bf Rat Basophilic Leukemia Cell Homogenate (RBL-1) serves as a 5-lipoxygenase enzyme source. The enzyme is incubated with [1-$^{14}$C]-arachidonic acid and Ca$^{++}$ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the $IC_{50}$ value.

Test C- Inhibition of slow reacting substance (SRS) biosynthesis in cells. SRS synthesis by Rat Basophilic Leukemia Cell (RBL-1) cells is induced by incubation of cells with ionophore A23187 alone and in combination with the test compound. The SRS released into the culture media is measured by high pressure liquid chromatography, scintillation counting or bioassay. In the bioassay procedure, the percent inhibition of SRS production is estimated by determining the doses of treated and control media needed in the tissue bath to produce equivalent contractions of segments of isolated guinea pig ileum. A compound that inhibits SRS biosynthesis by 50% or more is considered active at that concentration if an equivalent amount of the compound does not antagonize ileum contraction by SRS directly. If the compound directly inhibits the smooth muscle contractions, it will be considered inactive as an SRS biosynthesis inhibitor. Initial screening doses of test compounds are $1 \times 10^{-4}$M and $1 \times 10^{-5}$M.

Test-D- In vitro inhibition of human platelet 12-lipoxygenase. A 40,000 $\times$g supernatant of platelet lysate is incubated with [1-$^{14}$C]-labeled arachidonic acid in the presence and absence of test compound. The conversion product, 12-hydroxyeicosatetraenoic acid (12-HETE), is quantitated after isolation by thin-layer chromatography. Compounds, initially screened at 100 $\mu$M concentration, which inhibit the synthesis of 12-HETE by 30% or more, are considered active. $IC_{50}$ values are determined for active compounds.

Test E- In vitro inhibition of sheep seminal vesicle microsome cyclooxygenase. Arachidonic acid cyclooxygenase reaction rates, in the presence or absence of test compounds, are determined by monitoring oxygen uptake. Compounds which inhibit at $10^{-4}$M are tested further to determine $IC_{50}$ values.

The following examples further illustrate the present invention.

EXAMPLE 1

Preparation of 3,5-bis(1,1-dimethylethyl)-4-hydroxyphenylthiocyanate

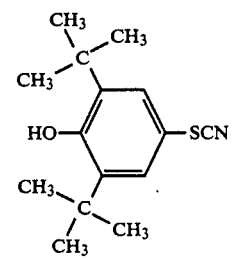

To a three-necked, round bottom 5 L flask, equipped with a mechanical stirrer, gas inlet, thermometer and gas inlet, thermometer and gas outlet, was added 2,6-di-tert-butylphenol (474 g, 2.30 mole), ammonium thiocyanate (76.12 g, 4.83 mole) and methanol (1200ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated from water, filtered and dried for 2 days over phosphorous pentoxide. The resulting gummy yellow solid was recrystallized from pentane and dried in vacuo to yield the product as a white powder, m.p. 61.5°-63° C. Analysis calc. for $C_{15}H_{21}NSO$: Theory: C, 68.40; H, 8.03; N, 5.32; S, 12.17. Found: C, 68.85; H, 8.05; N, 5.29; S, 12.12.

EXAMPLE 2

Preparation of 2,6-bis(1,1-dimthylethyl)-4-mercaptophenol

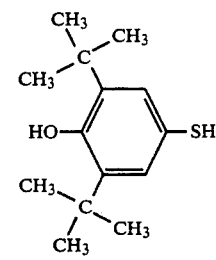

3,5-bis(1,1-Dimethylethyl)-4-hydroxyphenyl thiocyanate (55 g, 0.209 mold) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allows to warm to room temperature with stirring. The solution was concentrated, solvents removed, and the resulting oil chromatographed on silica. The fractions containing the thiol were combined, the solvents removed to yield a white powder which was recrystallized from methanol/water and dried to yield 43.3 g of the desired product. NMR confirmed the identity of the product.

EXAMPLE 3

Preparation of N,N-dicyclohexyl-2-propenamide

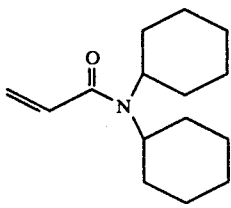

A solution of dicyclohexylamine (19.92 ml, 0.10 mole) and triethylamine (27.88 ml, 0.20 mole) in ethyl ether (100 ml) was cooled to 0° C. A solution of acryloyl chloride (7.93 ml, 0.1 mole) in ethyl ether (20 ml) was added and the solution was stirred for 12 hours, filtered and concentrated to obtain the product as a solid which was dried in vacuo. The stucture was confirmed by NMR.

EXAMPLE 4

Preparation of
3-[[3,5-bis(1,1-dimethylethyl)-4-hydroxyphenyl]thio]-N,N-dicyclohexylpropanamide

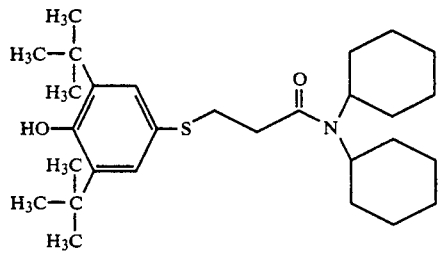

The title compound of Example 3 (1.9 g, 0.008 mole), 2,6-bis(1,1-dimethylethyl)-4-mercaptophenol(2 g, 0.008 mole) and triethylamine (0.5 ml) were stirred in methanol (25 ml) for about 12 hours. The solvent was removed in vacuo on a rotary evaporator, the crude material purified by chromatography on silica and recrystallized from hexane, m.p. ca. 168.5°–172° C. Analysis calc. for $C_{29}H_{47}O_2NS$(473.76): Calc.: C, 73.52; H, 10.00; N, 2.96; S, 6.77. Found: C, 73.43; H, 10.24; N, 2.91; S, 6.91.

EXAMPLE 5

Preparation of
N-tricyclo[3.3.1.1$^{3,7}$]dec-1-yl-2-propenamide

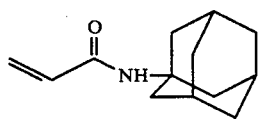

A solution of acryloyl chloride (4.05 ml, 0.05 mole) in ethyl ether (25 ml) was added to a cold (+5° C.) soltuion of 1-adamantaneamine (7.65 g, 0.05 mole) and triethylamine (15.3 ml, 0.11 mole) in ethyl ether (300 ml) and the solution stirred for 72 hours at room temperature. The solvent was removed on a rotary evaporator. The residue was dissoled in ethyl acetate (100 ml), washed with 10 percent hydrochloric acid (100 ml) and water (50 ml), dried over sodium sulfate, filtered and the solvent removed in vacuo leaving an oily solid which was crystallized from methanol-ethyl acetate-hexane. The structure was confirmed by NMR.

EXAMPLE 6

Preparation of
3-[[3,5-bis(1,1-dimethylethyl)-4-hydroxyphenyl]thio]-N-tricyclo[3.3.1.1$^{3,7}$]dec-1-ylpropanamide

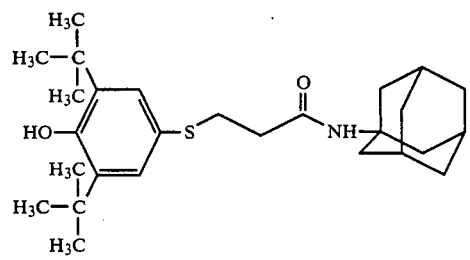

Following the method of Example 4, 2,6-bis(1,1-dimethylethyl)-4-mercaptophenol (1.19 g, 0.005 mole), the title compound of Example 5 (1.03 g, 0.005 mole) and triethylamine (0.5 ml) were stirred in methanol (100 ml) for 12 hours at room temperature under argon. The solvent and triethylamine were removed on a rotary evaporator and the product purified by chromatography on silica, recrystallized from ethyl aceate/hexane, filtered and dried in vacuo, m.p. ca.172.5°–173.5° C. Analysis calc. for $C_{27}H_{41}NO_2S$(443 69): Calc.: C, 73.09; H, 9.31; N, 3.16; S, 7.23. Found: C, 73.03; H, 9.18; N, 3.08; S, 7.30.

EXAMPLE 7

Preparation of
N-(6,6-dimethylbicyclo[3.1.1]hept-2-yl)-2-propenamide

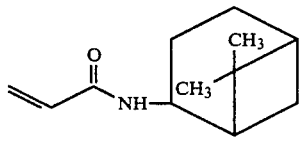

Following the procedure of Example 3, a solution of acryloyl chloride (4.05 ml, 0.05 mole) in ethyl ether (50 ml) was added dropwise to a cold 5° C. mixture of triethylamine (15.3 ml, 0.11 mole) and norpinylamine (6.96 ;g, 0.05 mole) in ethyl ether (400 ml). The reaction was allowed to warm to room temperature and stirred for 72 hours. The light tan solid was filtered and washed well with ethyl ether. The solvent and triethylamine were removed, leaving the title product as an oily solid. The sturcture was confirmed by NMR. Analysis calc. for $C_{12}H_{19}NO$(193.28): Calc.: C, 74.57; H, 9,91; N, 7.24. Found: C, 74.28; H, 9.65; N, 7.15.

EXAMPLE 8

Preparation of
3-[[3,5-bis(1,1-dimethylethyl)-4-hydroxyphenyl]thio]-N-(6,6-dimethylbicyclo[3.1.1]hept-2-yl)propanamide

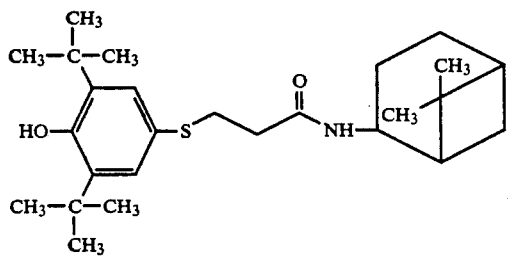

Following the method of Example 4, 2,6-(bis-1,1-dimethylethyl)-4-mercaptophenol (1.19 g, 0.005 mole), N-(6,6-dimethylbicyclo[3.1.1]hept-2-yl)-2-propenamide (0.96 g, 0.005 mole) and triethylamine (0.5 ml) were stirred in methylene chloride (75 ml) for 1 hours. Additional thiol (1 g) was Triethylphosphine (0.5 ml) was added and the solution stirred for 72 hours. The solvent and phosphine were removed on a rotary evaporator and the product purified by chromatography on silica and recrystallized from ethyl acetate/hexane, m.p. 152.5°–154° C. Analysis calc. for $C_{26}H_{41}NO_2S(431.68)$: Calc.: C, 72.34; H, 9.55; N, 3.24; S, 7.43. Found: C, 72.54; H, 9.53; N, 3.20; S, 7.58.

EXAMPLE 9

Preparation of
N-endo-bicyclo[2.2.1]hept-2-yl-2-propenamide

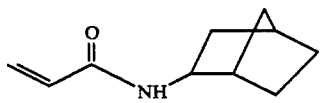

Following the method of Example 7, a solution of acryloyl chloride (2 ml, 0.025 mole) in ethyl ether was added to a mixture of endo-2-aminonorbornane (3.67 g, 0.025 mole) and triethylamine (15.3 ml) in methylene chloride (250 ml) and ethyl ether (250 ml) at 0°–5° C. over a 30 minute period. The solution was allowed to warm to room temperature and stirred for 72 hours. The solvents were evaporated on a rotary evaporator, fresh methylene chloride (400 ml) added and the solution refluxed for 3 hours. The solvents were removed on a rotary evaporator and the residue taken up in ethyl ether (500 ml), stirred for 1 hour, and the solid filtered and washed with ethyl ether. Removal of the solvent left the title product as an oil. The structure was confirmed by NMR.

EXAMPLE 10

Preparation of
N-endo-bicyclo[2.2.1]hept-2-yl-3-[[3,5-bis(1,1-dimethylethyl)-4-hydroxyphenyl]thio]propanamide

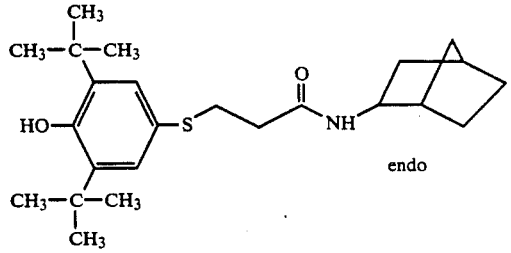

Following the method of Example 4, the title compound of Example 9 (0.87 g. 0.005 mole). 2,6-(bis-1,1-dimethylethyl)-4-mercaptophenol (1.19 g, 0.005 mole), triethylamine (0.5 ml) and triethylphosphine (0.5 ml) were stirred in methylene chloride (75 ml) for 12 hours. The solvent was removed on a rotary evaporator and the product purified by chromatography on silica, recrystallized from ethyl acetate/hexane, and dried, m.p. 128°–131° C. Analysis calc. for $C_{24}H_{37}NO_2(403.62)$: Calc.: C, 71.42; H, 9.24; N, 3.47; S, 7.94. Found: C, 71.69; H, 9.15; N, 3.46; S, 8.12.

EXAMPLE 11

Preparation of N-tricyclo[$3.3.1.1^{3,7}$]dec-2-yl-2-propenamide

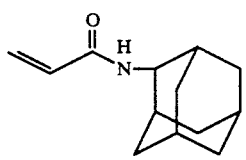

A solution of acryloyl chloride (4.52 g, 0.05 mole) in ethyl ether (20 ml) was added dropwise to a stirring mixture of 2-adamantylamine hydrochloride (9.35 g, 0.05 mole) and triethylamine (30.65 ml) in methylene chloride (200 ml) and ethyl ether (200 ml) over a 30 minute period. The solution was stirred for 12 hours, the solid filtered and washed with ethyl ether and the filtrate stripped to an oily material which was taken up in ethyl acetate and hexane and allowed to stand overnight. The solid was filtered, the filtrate concentrated and chilled and the product as an orange solid filtered and dried. The structure was confirmed by NMR.

EXAMPLE 12

Preparation of 3-[[3,5-bis(1,1-dimethylethyl)-4-hydroxyphenyl]thio]-N-tricyclo[3.3.1.1³,⁷]dec-2-yl propanamide

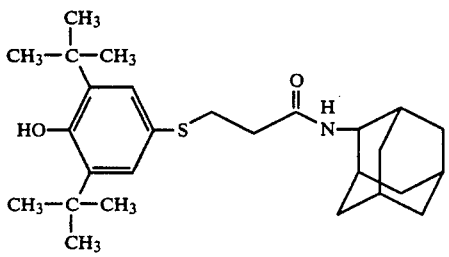

Following the procedure of Example 4, triethylamine (0.5 ml) was added to a solution of 2,6-bis(1,1-dimethylethyl)-4-mercaptophenol (1.19 g, 0.005 mole) and the N-tricyclo[3.3.1.1³,⁷]dec-2-yl-2-propenamide (1.02 g, 0.005 mole) in methanol (100 ml) and the solution stirred ar room temperature for 12 hours. The solvent and triethylamine were removed on a rotary evaporator and the product purified by chromatography on silica, recrystallized from ethyl acetate/ethyl ether/hexane and dried, m.p. ca. 155.5°–156° C. Analysis calc. for $C_{27}H_{41}NO_2S$(443.69): Calc.: C, 73.09; H, 9.31; N, 3.16; S, 7.35. Found: C, 73.18; H, 9.23; N, 3.09; S, 7.21.

EXAMPLE 13

Preparation of 3-(1-oxo-2-propenyl)-3-azabicyclo[3.2.2]- nonane

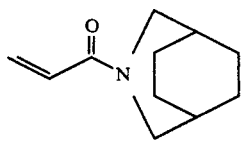

A solution of acryloyl chloride (4.05 ml, 0.05 mole) in 50 ml of ethyl ether was added with stirring to a cold mixture of 3-azabicyclo[3.2.2]nonane (6.26 g, 0.05 mole) and triethylamine (15.3 ml, 0.11 mole) in 250 ml of ethyl ether. The ice bath was removed and the reaction was allowed to warm to room temperature and stirred for 72 hours. The resulting white material was filtered and washed well with ethyl ether and ethyl acetate. The solvent was removed on a rotary evaporator and the residue taken up in ethyl ether, hexane added and the solution chilled. The remaining small amount of insoluble material was filtered and the solvent evaporated, leaving the product as an oil. The structure was confirmed by NMR.

EXAMPLE 14

Preparation of [3-[[3,5-bis(1,1-dimethylethyl)-4-hydroxyphenyl]thio]-1-oxopropyl]-3-azabicyclo[3.2.2]nonane

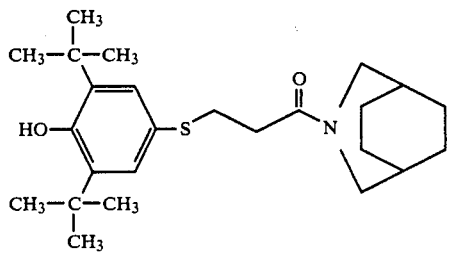

2,6-bis(1,1-Dimethylethyl)-4-mercaptophenol (1.19 g, 0.005 mole), 3-(1-oxo-2-propenyl)-3-azabicyclo[3.2.2-]nonane (900 mg, 0.005 mole) and triethylamine (1.25 ml) were combined following the procedure of Example 4 and stirred in methanol (50 ml) under an argon atmosphere for 72 hours. The product was purified by chromatography on silica and recrystallized from ethyl acetate and hexane, m.p. ca. 110.5°–112° C. Analysis calc. for $C_{25}H_{39}NO_2S$(417.65): Calc.: C, 71.90; H, 9.41; N, 3.35; S, 7.68. Found: C, 71.94; H, 9.27: N, 3.31; S, 7.88.

EXAMPLE 15

Preparation of 4-[[3,5-bis(1,1-dimethylethyl)-4-hydroxy phenyl]thio]butanoic acid

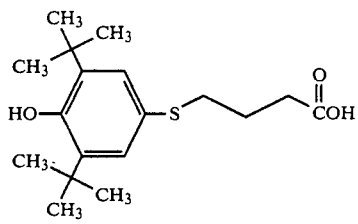

Potassium hydroxide flakes (2.52g, 0.045 mole) were added to a clear solution of 2,6-bis(1,1-dimethylethyl)-4-mercaptophenol (3.57 g. 0.0165 mole) and ethyl-4-bromo-butyrate (3.23 g, 0.0165 mole) in acetone (10 ml). Water (20 ml) was added and the solution stirred for 1.5 hours, the solvent removed on a rotary evaporator and water (50 ml) added, and the mixture was extracted with ethyl ether (3×75 ml). The aqueous layer was acidified with concentrated hydrochloric acid, extraced with ethyl ether (2×50 ml), the combined organic extracts were washed with water (50 ml), dried over sodium sulfate, filtered and the solvents removed, leaving an oil, which was purified by chromatography on silica, recrystallized from ethyl ether/Skellysolve B, filtered and the product dried in vacuo at room temperature for 12 hours, m.p. ca. 112°–113.5° C.

Analysis calc. for $C_{18}H_{28}O_3S$(324.48): Calc.: C, 66.63; H, 8.70; S, 9.88. Found: C, 66.71; H, 8.74; S, 9.57.

EXAMPLE 16

Preparation of 4-[[3,5-bis(1,1-dimethylethyl)-4-hydroxyphenyl]thio-N-tricyclo[3.3.1.1³,⁷]dec-1-yl butanamide

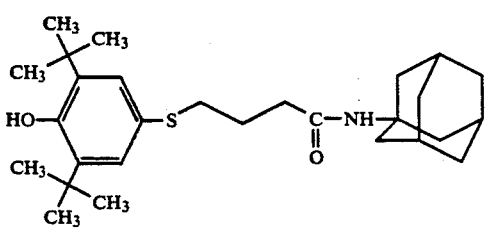

The title compound of Example 19 is dissolved in benzene and the solution cooled to about 5° C. in an ice bath. A solution of oxalyl chloride in benzene is added dropwise over a period of about 5 minutes. The ice bath is removed and the solution is allowed to warm to room temperature and is stirred for about 5 hours. The benzene is evaporated and fresh benzene is added. Triethylamine an 1-adamantaneamine are added to the solution and stirred overnight. The benzene is evaporated on a rotary evaporator and the product is purified by chromatography on silica.

EXAMPLE 17

Preparation of N-1-Azabicyclo[2.2.2]oct-3-yl-2-chloroacetamide, monohydrochloride

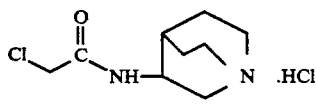

Potassium hydroxide (10 g) was added to a solution of 3aminoquinuclidine dihydrochloride (10.45 g, 0.052 mole) in water (80 ml) saturated with sodium chloride. After stirring for 30 minutes, methylene chloride (75 ml) was added and the layers separated. The aqueous layer was washed with methylene chloride (2×75 ml), and the extracts combined with the methylene chloride layer above; dried over sodium sulfate, filtered, and the volume reduced to 100 ml. A solution of chloroacetyl chloride (3.11 g, 0.0273 mole) in methylene chloride (25 ml) was added dropwise and the mixture stirred overnight. The solvent was removed on a rotary evaporator. The residue was recrystallized from methanol-ethyl acetate to give a white solid (4.7 g), m.p. ca. 189°-195° C. The structure was confirmed by NMR.

EXAMPLE 18

Preparation of N-1-Azabicyclo[2.2.2]oct-3-yl-2-[[3,5-bis(1,1-dimethylethyl)-4-hydroxyphenyl]thio]acetamide, monohydrochloride

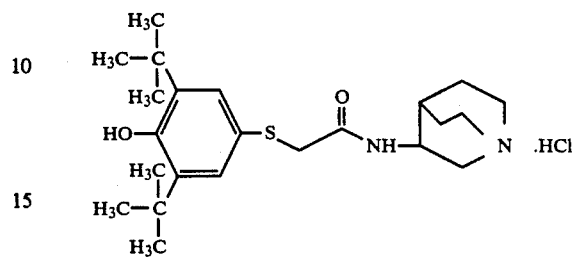

The title compound was prepared by dissolving the product of Example 17 (2.0 g, 0.0084 mole) and 2,6-bis (1,1-dimethylethyl)-4-mercaptophenol (1.99 g, 0.0084 mole) in acetonitrile (25 ml). Triethylamine (5 ml) was added to the mixture and the mixture stirred at room temperature for 12 hours then refluxed for 72 hours. The hot mixture was filtered and the solvent removed on a rotary evaporator. The residue was triturated with hexane and dissolved in hot ethyl acetate and allowed to cool. After filtering, the solvent was removed by a rotary evaporator and the residue recrystallized from ethyl acetate-methanol-ethyl ether to give a tan solid. The structure was confirmed by mass spectroscopy M+ 404.

EXAMPLES 19-24

By sutstituting the appropriate amide, e.g., N,N-dicyclohexyl-2-butenamide for the amide of Example 4, the following compounds are obtained:

Example 19: 3-[[3,5-bis(1,1-dimethylethyl)-4-hydroxyphenylthio]-N,N-dicyclohexylbutanamide.
Example 20: 2-[[3,5-bis(1,1-dimethylethyl)-4-hydroxyphenyl]thio-N,N-dicyclohexylacetamide.
Example 21: 2-[[3,5-bis(1,1-dimethylethyl)-4-hydroxyphenyl]thio-N-tricyclo[3.3.1.1³,⁷]dec-1-yl hexanamide.
Example 22: 4-[[3,5-bis(1,1-dimethylethyl)-4-hydroxyphenyl]thio]-N-(6,6-dimethylbicyclo[3.1.1]hept-2-yl)2,2-dimethylbutanamide.
Example 23: N-endo-bicyclo[2.2.1]hept-2-yl-2-[[3,5-bis (1,1-dimethylethyl)-4-hydroxypheny]thio]ethanamide.
Example 24: 3-[[3,5-bis(1,1-dimethylethyl)-4-hydroxyphenyl]thio]-N-tricyclo[3.3.1.1³,⁷]dec-2-yl)hexanamide.

EXAMPLE 25

Preparation of 3,5-dichloro-4-hydroxyphenyl thiocyanate

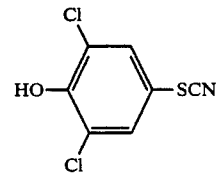

2,6-Dichlorophenol (100 g, 0.613 mole) and ammonium thiocyanate (102.73 g 1.350 mole) were mixed in methanol and the solution cooled to 0° C. Chlorine gas was bubbled through the reaction, maintaining the temperature below 10° C. The solution turned a pale yellow color. The reaction was stirred for a total of 3 hours until acidic at which time ammonia gas was bubbled through the reaction mixture and the solution stirred for an addtional three hours 0° to 10° C. The reaction was poured into iced distilled water, and filtered, yielding approximately 20 g of yellow solid which was dried overnight in vacuo. The filtrate was extracted with ethyl ether and the extract dried over magnesium sulfate and solvent removed in vacuo to yield approximately 100 g of crude product. Following purification by silica chromatography, the material was taken up in 1 liter of toluene, charcoal added, filtered and recrystallized from hexane to yield 55.03 g of product as yellow solid, m.p. ca. 94.5°-97° C. The structure was confirmed by NMR.

EXAMPLE 26

Preparation of 3,5-dichloro-4-mercaptophenol

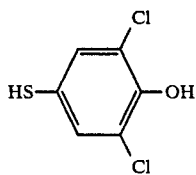

The title compound of Example 25 (55.03 g, 0.25 mole) was dissolved in 300 ml of acetone. Water 9 ml, 0.50 mole) was added and the solution cooled to 0° C. Triethyl phosphine (36.9 ml, 0.250 mole) was added dropwise over a period of 65 minutes, maintaining the temperature, stirred for 1½ hours, solvent was removed and the product purified by chromatography on silica and recrystallized from hexane to yield the title compound. Analysis calc. for $C_6H_4OCl_2S$: Calc.: C, 36.94; H, 2.07; Cl, 36.35; S, 16.44. Found: C, 36.96; H, 2.06; Cl, 36.31; S, 16.56.

EXAMPLES 27-30

By replacing 2,6-bis(dimethylethyl)-4-mercaptophenol with an appropriate dihalothiol such as 3,5-dichloro-4-mercaptophenol in the preceding Examples, the corresponding dihalo amides are obtained:

Example 27: 3-[[3,5-dichloro-4-hydroxyphenyl]thio]-N-tricyclo[3.3.1.1³,⁷]dec-1-yl propanamide.

Example 28: N-endo-bicyclo[2.2.1]hept-2-yl-3-[(3,5-dichloro-4-hydroxyphenyl)thio]propanamide.

Example 29: 3-[[3,5-dichloro-4-hydroxyphenyl]thio]-N-tricyclo[3.3.1.1³,⁷]dec-2-yl propanamide.

Example 30: [3-[(3,5-dichloro-4-hydroxypheny)thio]-1-oxopropyl]-3-azabicyclo[3.2.2]nonane.

EXAMPLE 31

Preparation of 2'-hydroxy1,1':3',1''-terphenyl]-5'-yl thiocyanate

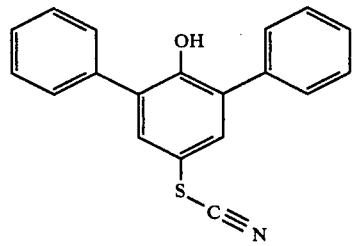

2,6-Diphenylphenol (100.0 g, 0.406 mole) and ammonium thiocyanate (76.99 g, 0.893 mole) were suspended in methanol (150 ml) in a three-necked round bottom flask equipped with magnetic stirrer, thermometer and gas inlet tube. The reaction mixture was cooled to −5° C. in an acetone/ice bath and chlorine gas bubbled through the solution for three hours. Maintaining the temperature below 10° C., ammonia gas was bubbled through the reaction for 2 hours. The contents of the flask were then poured into iced distilled water (250 ml) and allowed to stand for 12 hours in the refrigerator. After filtering, the solid was dried in vacuo at 45° C. for 12 hours. The title compound was purified by chromatography on silica and recrystallized from hexane, m.p. about 104°-106.5° C.

Analysis calc. for $C_{19}H_{13}OSN(303.39)$: Calc.: C, 75.22; H, 4.32; N, 4.62; S, 10.57. Found: C, 75.12; H, 4.49; N, 4.65; S, 10.41.

EXAMPLE 32

Preparation of 5'-mercapto[1,1':3',1''terphenyl]-2'-ol

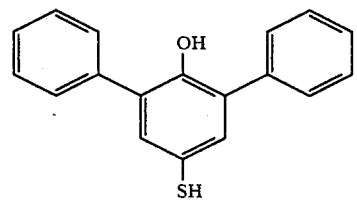

The title compound of Example 31 (32.2 g, 0.106 mole) was dissolved in acetone (150 ml) and water (1.9 ml), stirred and cooled to −5° C. Triethylphosphine (15.7 ml, 0.106 mole) was added dropwise over a period of 40 minutes. The raction was stirred at 0° for 1 hour and then at room temperature for 2 hours. The solvent was evaporated and the product isolated by chromatography on silica.

Analysis calc. for $C_{18}H_{14}OS(278.31)$: Calc.: C, 77.67; H, 5.07; S, 11.52. Found: C, 77.80; H, 5.19; S, 11.68.

EXAMPLES 33-38

By replacing 2,6-bis(1,1-dimethylethyl)-4-mercaptophenol in Examples 4, 6, 8, 10, 12, 14, 16, 18, and 19-24 with the product of Example 32, the corresponding 3,5-diphenyl products are obtained:

Example 33: 3-[(2'-hydroxy[1,1':3',1''-terphenyl]-5'-yl) thio]-N,N-dicyclohexylpropanamide.

Example 34: 3-[(2'-hydroxy[1,1':3',1''-terphenyl]-5'-yl) thio]-N-tricyclo3.3.1.1³,⁷]dec-1-yl propanamide.

Example 35: 3-(2'-hydroxy[1,1':3',1''terphenyl]-5'-yl)thio]-N-(6,6-dimethylbicyclo [3.1.1]hept-2-yl)propanamide.

Example 36: N-endo-bicyclo[2.2.1]hept-2-yl-4-[(2'-hydroxy [1,1':3',1''-terphenyl]5'-yl)thio]butanamide.

Example 37: 3-(2'-hydroxy[1,1':3',1''-terphenyl]-5''-yl) thio]-N-tricyclo[3.3.1.1$^{3,7}$]dec-2-yl propanamide.

Example 38: [3-[(2'-hydroxy[1,1':3',1''-terphenyl]-5'-yl) thio]-1-oxopropyl]-3-azabicyclo-[3.2.2]nonane.

The active agents of this invention can be administered to animals, including humans, as pure compounds. However, it is advisable to first combine one or more of the active compounds with one or more suitable pharmaceutically acceptable carriers or diluents to attain a satisfactory size to dosage relationship and thereby obtain a pharmaceutical composition.

Pharmaceutical carriers which are liquid or solid can be employed. Solid carriers such as starch, sugars, talc and the like can be used to form powders which may be used for direct administration or to fill gelatin capsules. Suitable lubricants such as magnesium stearate, stearic acid, as well as binders and disintegrating agents may be included to form tablets. Additionally, flavoring and sweetening agents may be added.

Unit dosage forms such as tablets and capsules can contain any suitable, predetermined, therapeutically effective amount of one or more active agents and a pharmaceutically acceptable carrier or diluent. Generally speaking, solid oral unit dosage forms of a compound of this invention will contain from 1.75 to 750 mg per tablet of drug.

The compounds of this invention exhibit both oral and parenteral activity and accordingly can be formulated in dosage forms for either oral or parenteral administration.

Solid oral dosage forms include capsules, tablets, pills, powders, granules and the like.

Liquid dosage forms for oral administration include emulsions, suspensions, solutions, syrups and the like containing diluents commonly used in the art such as water. Besides inert diluents, such preparations can also include adjuvants such as wetting agents, emulsifying and suspending agents, and sweetening, flavoring and perfuming agents.

Preparations for parenteral administration include sterile aqueous or non-aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The compounds of this invention may also be formulated for topical or transdermal application using carriers which are well known in the art, as well as in aerosols or sprays for nasal administration.

The amount of active ingredient administered may be varied; however, it is necessary that the amount of active ingredient be such that a suitable dosage is given. The selected dosage depends upon the desired therapeutic effect, the route of administration and the duration of treatment. Generally speaking, oral dosages of from 0.1 to 100 mg/kg, and preferably from 0.5 to 50 mg/kg of body weight daily are administered to patients in need of such treatment, preferably in divided dosages, e.g. three to four times daily. In the case of acute allergic or hypersensitivity reactions, it is generally preferable to administer the initial dosage via the parenteral route, e.g. intravenous, and continue parenteral administration until the patient is stabilized, and can be maintained, if necessary on oral dosing.

In the case of psoriasis and other skin conditions, it is preferred to apply a topical preparation of a compound of this invention to the affected areas three or four times daily.

In treating asthma and arthritis with a compound of this invention, the compounds may be administered either on a chronic basis, or as symptoms appear. However, in the case of arthritis and other inflammatory conditions which can lead to deterioration of joints and malformations, it is generally preferable to administer the active agent on a chronic basis.

When the compounds of this invention are co-administered with one or more cyclooxygenase inhibitors, they may conveniently be administered in a unit dosage form or may be administered separately. When the patient is allergic or hypersensitive to the cycloxygenase inhibitor, it is preferred to initiate therapy with a compound of this invention prior to administration of the cyclooxygenase inhibitor.

A typical tablet of this invention can have the following composition:

| Ingredient | Mg/tablet |
| --- | --- |
| Active ingredient | 100 |
| Starch, U.S.P. | 57 |
| Lactose, U.S.P. | 73 |
| Talc, U.S.P. | 9 |
| Stearic acid | 12 |

It will be understood by those skilled in the art that the above examples are illustrative, not exhaustive, and that modifications may be made without departing from the spirit of the invention and the scope of the claims.

The invention claimed is:

1. A compound of the formula

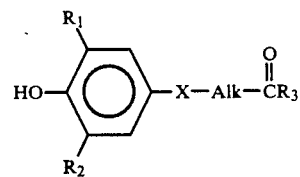

wherein $R_1$ and $R_2$ are the same or different members of the group consisting of phenyl, substituted phenyl and a

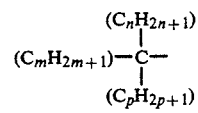

group wherein n, m and p are independently an integer of from 1 to 8 provided that $n+m+p$ is equal to or less than 10; X is thio or sulfinyl; Alk is straight or branched chain lower alkylene, and $R_3$ is selected from the group consisting of bicycloalkylamino, tricycloalkylamino, or dicycloalkylamino.

2. A compound of claim 1 wherein $R_1$ and $R_2$ each are

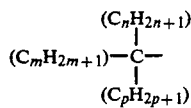

3. A compound of claim 2 wherein $R_1$ and $R_2$ each are 1,1-dimethylethyl.

4. A compound of claim 1 wherein $R_1$ and $R_2$ each are phenyl.

5. A compound of claim 1 wherein X is thio.

6. A compound of claim 1 wherein X is sulfinyl.

7. A compound of claim 1 wherein X is thio.

8. A compound of claim 7, 3-[[3,5-bis(1,1-dimethylethyl)-4-hydroxyphenyl]thio]-N,N-dicyclohexylpropanamide.

9. A compound of claim 7, 3-[[3,5-bis(1,1-dimethylethyl-4-hydroxyphenyl]thio]-N-(6,6-dimethylbicyclo-[3.1.1]hept-2-yl) propanamide.

10. A compound of claim 7, N-endo-bicyclo-[2.2.1]hept-2-yl-3-[[3,5-bis(1,1-dimethylethyl)-4-hydroxypheny]thio]propanamide.

11. A compound of claim 7, 3-[[3,5-bis(1,1-dimethylthyl)-4-hydroxyphenyl]thio]-N-tricyclo[$3.3.1.1^{3,7}$]dec-2-yl propanamide.

12. A compound of claim 7 which is 3-[[3,5-bis(1,1-dimethylethyl)-4-hydroxyphenyl]thio]-N-tricyclo [$3.3.1.1^{3,7}$]dec-1-yl propanamide.

13. A pharmaceutical composition for the treatment of inflammation and allergy comprising a therapeutically effective amount of a compound according to claim 1 and a pharmaceutically acceptable carrier.

* * * * *

UNITED STATES PATENT AND TRADEMARK OFFICE
CERTIFICATE OF CORRECTION

PATENT NO. : 5,019,597

DATED : May 28, 1991

INVENTOR(S) : Mueller, et. al.

Page 1 of 3

It is certified that error appears in the above-identified patent and that said Letters Patent is hereby corrected as shown below:

Column 1, line 1, reading "BICYCLOALKYL TRICYCLOALKYL" should read -- BICYCLOALKYL, TRICYCLOALKYL --.

Column 1, line 49, reading "inflammatory site. Whether" should read -- inflammatory site, whether --.

Column 4, line 19, reading "is preferably hydrolized to" should read -- is preferably hydrolyzed to --.

Column 5, line 22, reading "fraction bf Rat Basophilic" should read -- fraction of Rat Basophilic --.

Column 6, line 65, reading "and the reaction was then allows" should read -- and the reaction was then allowed --.

Column 7, line 66, reading "was added to a cold (+5° C.) soltuion of" should read -- was added to a cold (+5° C.) solution of --.

Column 8, line 38, reading "(443 69)" should read -- (443.69) --.

Column 8, line 60, reading "(6.96 ;g, 0.05 mole)" should read -- (6.96 g, 0.05 mole) --.

Column 8, line 66, reading "The sturcture" should read -- The structure --.

Column 8, line 67, reading "H, 9,91;" should read -- H, 9.91; --.

Column 9, line 26, reading "tional thio (1 g) was Triethylphosphine" should read -- tional thio (1 g) was added, the reaction stirred for an additional 12 hours. Triethylphosphine --.

UNITED STATES PATENT AND TRADEMARK OFFICE
CERTIFICATE OF CORRECTION

PATENT NO. : 5,019,597

DATED : May 28, 1991

INVENTOR(S) : Mueller, et al.

It is certified that error appears in the above-identified patent and that said Letters Patent is hereby corrected as shown below:

Column 13, line 50, reading "3aminoquinuclidine" should read -- 3-aminoquinuclidine --.

Column 14, line 39, reading "yphenylthio]-N,N" should read -- yphenyl]thio]-N,N --.

Column 14, line 41, reading "yphenyl]thio-N,N" should read -- yphenyl]thio]-N,N --.

Column 14, line 43, reading "yphenyl]thio-N,N-" should read -- yphenyl]thio]-N,N- --.

Column 14, line 67, reading "(102.73g 1.350 mole)" should read -- (102.73g, 1.350 mole) --.

Column 16, line 3, reading "Preparation of 2'-hydroxyl,1':3',1"" should read -- Preparation of 2'-hydroxy[1,1':3',1" --.

Column 16, line 53, reading "The raction was stirred" should read -- The reaction was stirred --.

Column 16, line 68, reading "-N-tricyclo3.3.1" should read -- -N-tricyclo[3.3.1 --.

Column 17, line 1, reading "Example 35: 3-2'-hydroxy[" should read -- Example 35: 3-[(2'-hydroxy[" --.

UNITED STATES PATENT AND TRADEMARK OFFICE
CERTIFICATE OF CORRECTION

PATENT NO. : 5,019,597

DATED : May 28, 1991

INVENTOR(S) : Mueller, et al.

It is certified that error appears in the above-identified patent and that said Letters Patent is hereby corrected as shown below:

Column 17, line 6, reading "Example 37: 3-2'hydroxy[" should read -- Example 37: 3-[(2'-hydroxy[" --.

Signed and Sealed this

Fifth Day of January, 1993

Attest:

DOUGLAS B. COMER

Attesting Officer

Acting Commissioner of Patents and Trademarks